United States Patent [19]

Hübner

[11] Patent Number: 4,569,223

[45] Date of Patent: Feb. 11, 1986

[54] METHOD OF AND APPARATUS FOR MULTIPLE DETECTOR MEASUREMENT OF AN ENVIRONMENTAL PARAMETER

[76] Inventor: Hans J. Hübner, Katthagen 24,, 4400 Münster, Fed. Rep. of Germany

[21] Appl. No.: 635,323

[22] Filed: Jul. 27, 1984

[30] Foreign Application Priority Data

Jul. 28, 1983 [DE] Fed. Rep. of Germany ....... 3327153

[51] Int. Cl.$^4$ ............................................ G01N 31/00
[52] U.S. Cl. ........................................................ 73/23
[58] Field of Search ................... 73/23, 1 G; 340/632, 340/633, 634; 364/571, 582, 580, 497, 498; 422/94, 98

[56] References Cited

U.S. PATENT DOCUMENTS

| | | | |
|---|---|---|---|
| 3,427,862 | 2/1969 | Hubner | 73/23 |
| 3,845,288 | 10/1974 | Cornyn, Jr. et al. | 364/582 |
| 4,231,249 | 11/1980 | Zuckerman | 73/23 |
| 4,369,647 | 1/1983 | Shigemori et al. | 340/634 |
| 4,464,653 | 8/1984 | Winner | 73/23 |
| 4,475,378 | 10/1984 | Boutonnat et al. | 340/634 |
| 4,485,666 | 12/1984 | Higgins et al. | 73/23 |

FOREIGN PATENT DOCUMENTS

| | | |
|---|---|---|
| 3027051 | 2/1982 | Fed. Rep. of Germany . |
| 3138046 | 4/1982 | Fed. Rep. of Germany . |
| 3243542 | 5/1984 | Fed. Rep. of Germany . |
| 1564981 | 4/1980 | United Kingdom . |

OTHER PUBLICATIONS

"Ein Frei Programmierbares Mikroprozessorgesteuertes Datensystem" by D. Voigt, Published in Messen+Prüfen/Automatik—Jul./Aug. 1982.
"Grundlösungen Von Aufgaben Zur Weiterverarbeitung" by G. Strohrmann, Marl Published in Regelungstechnische Praxis 24. Jahrgang 1982 HEFT 8.
"Die Zuverlässigkeit Von Messsystemen" by Dr. P. Profos, Published in Handbuch der Industriellen Messtechnik (Vulkan—Verlag Dr. W. Classen Nachf. GmbH & Co. KG. Essen, 1978).
"Sicher Vor Allen Gasgefahren Durch Vabotector—Ex" Gas Messung (Gesellschaft Für GerätebaumbH & Co.KG) (6/1982 3000 B+M).

Primary Examiner—Stephen A. Kreitman

[57] ABSTRACT

Mine ventilating atmosphere parameters, e.g. methane concentration, can be measured according to the invention with an arrangement which has a continuously operating first measuring system to which a second measuring system is periodically connected to measure the same parameter with its output being utilized to control the zero point or sensitivity setting of the first measuring system.

16 Claims, 3 Drawing Figures

METHOD OF AND APPARATUS FOR MULTIPLE DETECTOR MEASUREMENT OF AN ENVIRONMENTAL PARAMETER

CROSS REFERENCE TO RELATED APPLICATIONS

This application is related to my commonly assigned copending application (now U.S. Pat. No. 4,526,028) Ser. No. 493,696 filed May 11, 1983 and entitled "Process and Device for Indicating and Evaluating Environmental Parameters." This application is based upon the German application No. P 32 17 798.4 filed May 12, 1982, both of the aforementioned applications being incorporated herein by reference. Reference may also be had to my concurrently filed copending application Ser. No. 635,329 and my concurrently filed copending application Ser. No. 635,324 and the German applications upon which these U.S. applications are based, all also incorporated by reference herein.

FIELD OF THE INVENTION

My present invention relates to a method of and to an apparatus for the measurement of evaluation of parameters of an environmental atmosphere, especially the concentration of a component of such an atmosphere and, more particularly to the measurement and evaluation of combustible or other gaseous components of a ventilation current or flow in a subterranean site such as a mine gallery.

BACKGROUND OF THE INVENTION

Gas analyzing equipment is utilized for many purposes and in many applications, an important one of which is the continuous measurement of a parameter of a subterranean atmosphere, e.g. the continuous monitoring of the concentration of a combustible and/or toxic component of an air current, an air stream ventilating a mine gallery or shaft.

Devices for this purpose may include a power source, e.g. a battery, a measuring system responsive to the parameter to be measured and actuating unit and a display, signalling or other data processing unit, i.e. a unit which responds to the information supplied by the measuring unit.

The measurement and evaluation of environmental parameters may be used for long term information gathering or even for short term information development which can be directly evaluated or can be stored for subsequent evaluation for any desired purpose.

The principal reason for using such systems in a mine or other subterranean environment is for safety, i.e. to alert mine personnel to a potentially dangerous situation, to initiate the evacuation of the mine or to trigger some remedial operation such as increased ventilation.

As a consequence, systems of the type described have been long used in such mining applications.

It is known, for example, to measure the concentration of explosive and combustible gases, such as fire damp or methane by a catalytic combustion measuring system, to measure toxic gas concentrations (e.g. carbon monoxide concentrations) by chemisorption on a metal oxide semiconductor, to measure oxygen concentrations by a chemical current generating system whereby the oxygen is involved in an electrolyte action, and to quantitatively determine carbon dioxide in a gas stream utilizing thermal conductivity phenomena (see the brochure 6/82 describing the "VABOTECTOR-EX" instrument marketed by the firm Gesellschaft fur Geratebau mbH & Co. KG of the German Federal Republic).

Indeed, various systems may be used for measuring a single parameter, for example, at different concentration ranges. The latter is the case where, for small percentages of methane in the atmosphere, the catalytic composition method can be used whereas, for higher concentrations which may exceed the lower explosive limit and where catalytic combustion may be dangerous, a thermal conductivity method may be applied.

Continuous measurements have also been carried out heretofore with different measuring systems. One of the problems with continuous measuring systems, at least in prior art applications, has been that the zero point, balancing and/or sensitivity tends to change significantly with time. Thus one may observe a change in the pitch or inclination of the measuring curve, variations in inflection points thereof, etc. This, or course, leads to a falsification of the measuring results.

Not all measuring systems are suitable in all applications. For example, some have a greater electric power demand than others so their use as power availability falls becomes less and less desirable. Consequently, one may wish to use one measuring system where the power availability is substantial and as power availability diminishes, to switch to another measuring system. These and other reasons, such as safety, accuracy, etc. require a variety of measuring systems to be available.

In my printed German patent document—open application No. DE-OS 32 43 542 (corresponding to German Patent Application No. P 32 43 542), which is not prior art as to this application but which is incorporated herein by reference, I have described a system utilizing different measuring systems for a given parameter in which one measuring system is utilized normally and the system is switched over to a second measuring system when an interruption in service of the first measuring system results or may result.

In this case a particularly sensitive and accurate measuring system for low concentration of methane was cut out and a less precise system substituted for it to maintain the reliability of the overall arrangement in detecting the advent of dangerous conditions in a mine. This application, however, did not deal with problems encountered with the shift in the characteristic curve reference levels, zero point or balance in a continuous measurement of such a parameter.

OBJECTS OF THE INVENTION

It is, therefore, the principal object of the present invention to provide an improved method of effecting continuous measurement of a parameter of an atmosphere, especially a gas concentration in a subterranean atmosphere, whereby disadvantages of earlier systems are obviated.

It is another object of the invention to improve the accuracy of continuous measurement systems so that the disadvantages enumerated do not obtain.

Yet a further object of this invention is to provide an improved apparatus for carrying out the method of the present invention.

SUMMARY OF THE INVENTION

These objects and others which will become apparent hereinafter are attained, in accordance with the present invention in a system for continuous measurement of and evaluation of a parameter of the environmental atmosphere especially a ventilating current of a mine gallery, shaft or other subterranean site, which comprises at least one continuous measurement system, hereinafter referred to as a first measurement system, providing a continuous monitoring of this parameter, e.g. a gas concentration, and at least one second measuring system which is activated at time-spaced intervals, preferably periodically, and means for comparing the measurement value produced by the first system with the measurement value of the second measuring system for determining the reliability of the first measuring system, i.e. for setting a functional state of the latter system.

Practically any continuously operating measuring system will be the subject sooner or later to changes in its functioning parameters and according to the invention by monitoring its functional state at predetermined time intervals, preferably periodically, based upon the output of a second measuring system, I am able to adjust the continuous first measuring system to restore it to its original state, preferably automatically. The measurement value obtained with the second measuring system can thus be used as a periodically available reference value for the operation of the first measuring system, if desired in the case where the value obtained by the second measuring system is sufficiently accurate.

The second measuring system can be a system which is not designed for or capable of continuous measurement and thus cannot be used as a substitute for the first measurement system for such continuous measurement.

For example, I am able to use for the continuous measurement system a cost effective device which may have less stability than a more expensive and/or more stable measuring system for the same parameter as long as the second system is of this latter type and is used to periodically correct the first system.

When reference is made herein to the magnitude of a parameter of the environmental atmosphere, while I preferably intend to thus designate concentrations of the various gases in the mine atmosphere and especially the concentrations of combustible or explosive gases such as fire damp/methane, I also intend to include in this general designation other parameters of the atmosphere such as the temperature, the relative humidity, the ventilating gas flow velocity or the gas pressure and like parameters.

However, in the best mode embodiment of the invention, it is the methane concentration in the mine atmosphere which will be measured.

The method and apparatus of the invention can utilize practically any reasonable period for the periodic recalibration of the continuous measuring system and I have found, for example, that such recalibration in most cases need not take place more than once a week in the monitoring of methane concentrations in mining applications. In that case, the apparatus of the invention automatically, i.e. through the use of a timer, will automatically activate the second measuring system at each recalibration time.

Naturally, means can be provided or I may monitor the operation of the continuous measuring system and in the event of failure of the latter, switch in the second measuring system for continuous measurement at least as a temporary measure until the failure of the first measuring system can be corrected in spite of the fact that the second measuring system may be more expensive. This, of course, improves the reliability of the system which thereby places safety foremost.

According to the invention, moreover, the recalibration of correction of the functioning of the first system, should a deviation be detected by the periodic comparison of its output with that of the second measuring system, can include a resetting of a zero point and/or a correction of the sensitivity of the first system effected by hand or more preferably, automatically.

Basically it is possible that both the first continuous measuring system and the second or periodically actuated correction measuring system, can operate utilizing one and the same measuring principle. This can be the case when the continuously operating first measuring system tends to saturate or have its measuring capacity change with time because of the prolonged use. In that case, the relatively briefly operated correction system will experience little likelihood of such saturation because of its number of periods of operation and can be utilized for recalibration of the first system over extremely long periods of time.

Naturally, if at any time the operation of the first system cannot be corrected within acceptable tolerance limits or the operation of the first system becomes unacceptable, the first system can be cut out and subjected to a regeneration treatment or some other restoration operation while the second measuring system takes up its continuous measurement function and, indeed, the first measuring system can then be operated periodically for monitoring the functional state of the second, now continuous measuring system. In the latter case utilizing relatively simple means and only two substantially identical measuring systems, I can obtain the benefit of continuous measurement with periodic monitoring of the measurement with alternation of the functions of the two systems.

In many cases it is not practical to either monitor the continuous measurement system by a measurement system operating in the same principle or to substitute the second measuring system operating in the same principle for the first. In that case, the second measuring system which is utilized for monitoring and correcting the first measuring system can be one which operates on a different measuring principle. Then the second measuring system generally will be a short-term measuring system which can be especially precise and even a considerably more expensive measuring system than the first or continuous system.

I have found that it is highly advantageous to provide the first and/or second measuring system as a multichannel measuring system, especially a $\frac{2}{3}$ multichannel measuring system, i.e. a system in which three inputs are provided and the best two values out of the three supplied by these inputs are utilized, i.e. are further processed. The two "best" data or information signals may be those which are closest to one another.

The use of such a multichannel measuring system is especially important for the second or correction measuring system whose precision can thereby be greatly enhanced.

In this manner the correction output of the second measuring system has a greater probability of absolute correctness and can be utilized for a corresponding correction of the first measuring system so that the overall system operates with far greater precision than would otherwise by the case.

In the German Patent Document No. DE-OS, 32 43 542, which as noted is not prior art to the present application and which was filed by me, there is described an automatic switchover from one measuring system to another measuring system when problems are encountered with the first measuring system under circumstances in which the second measuring system does not involve such problems.

In the case of the monitoring of methane concentrations, for example, the first system can use catalytic combustion of the combustible to measure concentrations up to a certain point, and beyond this point, where measurements with that system might become dangerous, the methane concentration can be measured utilizing the thermal conductivity method.

The present invention has been found to have especially effective applications in conjunction with that earlier system which is hereby incorporated in its entirety by reference to the German patent document (see also the aforementioned U.S. application Ser. No. 635,324.

A measuring unit in accordance with the invention which utilizes a first continuous measuring system and a second measuring system which is activated at predetermined time intervals, periodically, can be realized in a number of ways. For example, the first measuring system may include an adjustment unit for the adjustment or setting of a function parameter, especially the setting of the zero point and/or the sensitivity or slope of the characteristic curve. In this case, the second measuring system can have at its output an adjusting device for the first measuring system so that correction of the function parameter of the first measuring system is effected in accordance with the magnitude of the output of the second measuring system. Between the second measuring system and the control element for the function parameter of the first measuring system, I may connect a set point/actual value comparator so that the output signal of the first measuring system or its adjustment unit is connected to the actual valve input of the comparator, the output of the second measuring system is connected to the set point input of the comparator and the output of this comparator is connected to the adjustment unit of the first measuring system.

A multichannel measuring system is realizable in accordance with the present invention in that a plurality of second measuring systems, especially three such second measuring systems are connected in parallel to the inputs of a selector switch especially a ⅔ selector which can process the inputs to provide, for example, a mean value of the best two out of three inputs as described to the set point input of the comparator.

The second measuring system can, of course, be integrated in the measuring circuit or apparatus providing the first measuring system, the second measuring system being thereby permanently associated with the first measuring system. In this case, the second measuring system need only be switched on at predetermined times and the switching of the second measuring system can be effected centrally from a central computer or from a remote location or at the measurement site by hand or by a timer built into the circuitry or in the central unit.

It has been found to be preferable, however, to provide a second measuring system in a separate measuring unit which can be connected to the first measuring unit periodically or at selected time intervals by a control system or a signal transfer arrangement. One advantage of this arrangement is that it allows the second measuring unit to be connected and disconnected from the first measurement unit, to have its own power source and its own actuating and display device. A measuring system of this type can thus be used for a number of first measuring units, can be used for independent measurements if desired, and can be an especially expensive unit. For example a second measuring unit of this type can be connected over a period of a week with a number of first measuring units along a mine gallery or other subterranean structure.

BRIEF DESCRIPTION OF THE DRAWINGS

The above and other objects, features and advantages of the present invention will become more readily apparent from the following description, reference being made to the accompanying drawing in which.

SPECIFIC DESCRIPTION

Figure 1:
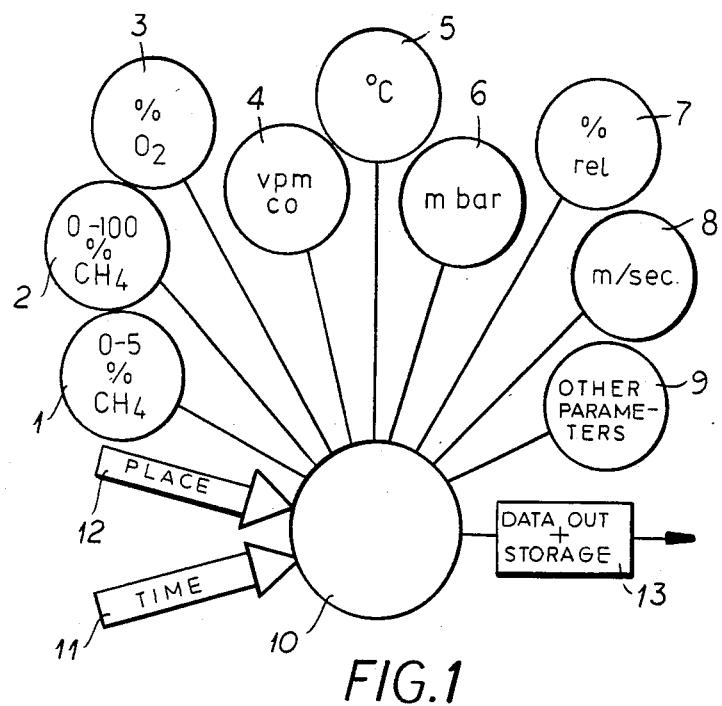
FIG. 1 is a function diagram of a system for the measurement and evaluation of parameters of the environment or atmosphere in a mine.

In the diagram of FIG. 1, as more fully described in Ser. No. 493,696, it can be seen that a multiplicity of parameters of the environmental atmosphere, e.g. a ventilation gas stream, in a mine gallery or other subterranean site, can be fed to the measuring device 10. These parameters include concentration parameters 1-4, the air temperature 5, the air pressure 6, the relative humidity 7 and the air velocity 8. The reference numeral 9 represents other parameters which may be relevant. Other inputs to the measuring device 10 include the time 11 and the place 12 at which the measurement is taken.

All of this data can be stored in a storage unit and can be transferred as represented at 13 to a central unit or computer not otherwise illustrated in this Figure.

More specifically, the concentration inputs 1 and 2 can include, respectively, inputs from a catalytic combustion methane concentration detector, which is effective at concentrations of 0 to 5%, and a thermal conductivity concentration detector which is effective for concentrations of methane from 0 to 100%. The latter may be replaced by an oxygen detector and appropriate calculating system as described in the concurrently filed copending application Ser. No. 635,329 filed July 27, 1984. The concentration input 3 is an oxygen detector, preferably of the chemical current-generating type while the concentration detector 4 is a carbon monoxide detector preferably operating on the chemisorption on metal oxide semiconductor principle.

Figure 2:
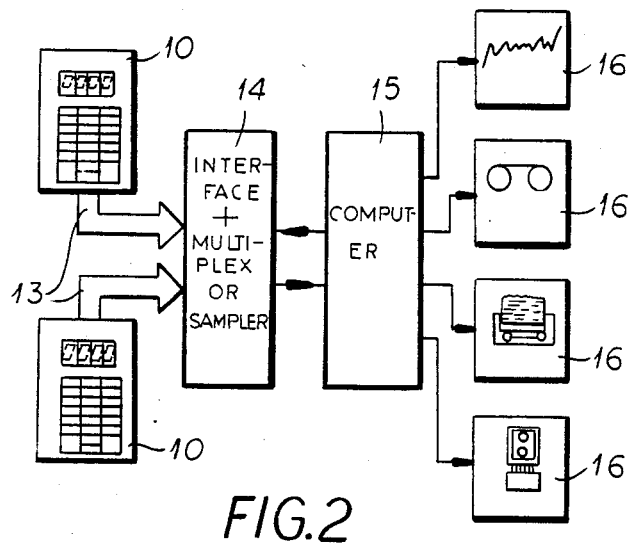
FIG. 2 is a block diagram of an apparatus for measuring and evaluating the parameters of the atmosphere.

FIG. 2 schematically illustrates how a large-scale apparatus can operate embodying the principles described.

Here two measuring units 10 are shown to have data outputs 13, these units 10 being representative of a large number of such units which can be spaced along a mine gallery and which can have their stored outputs, representing continuous measurement values, taped periodically by appropriate multiplexing for delivery to the concentration unit or computer 4. The signal transfer and sampling network is here represented at 14, the various peripherals associated with the computer have been represented at 16 and can include a display magnetic tape storage, the input, output terminal and a motor or other device for remote transmission of the data.

Reference may be had in this regard to the copending U.S. application Ser. No. 493,696 mentioned previously.

Figure 3:
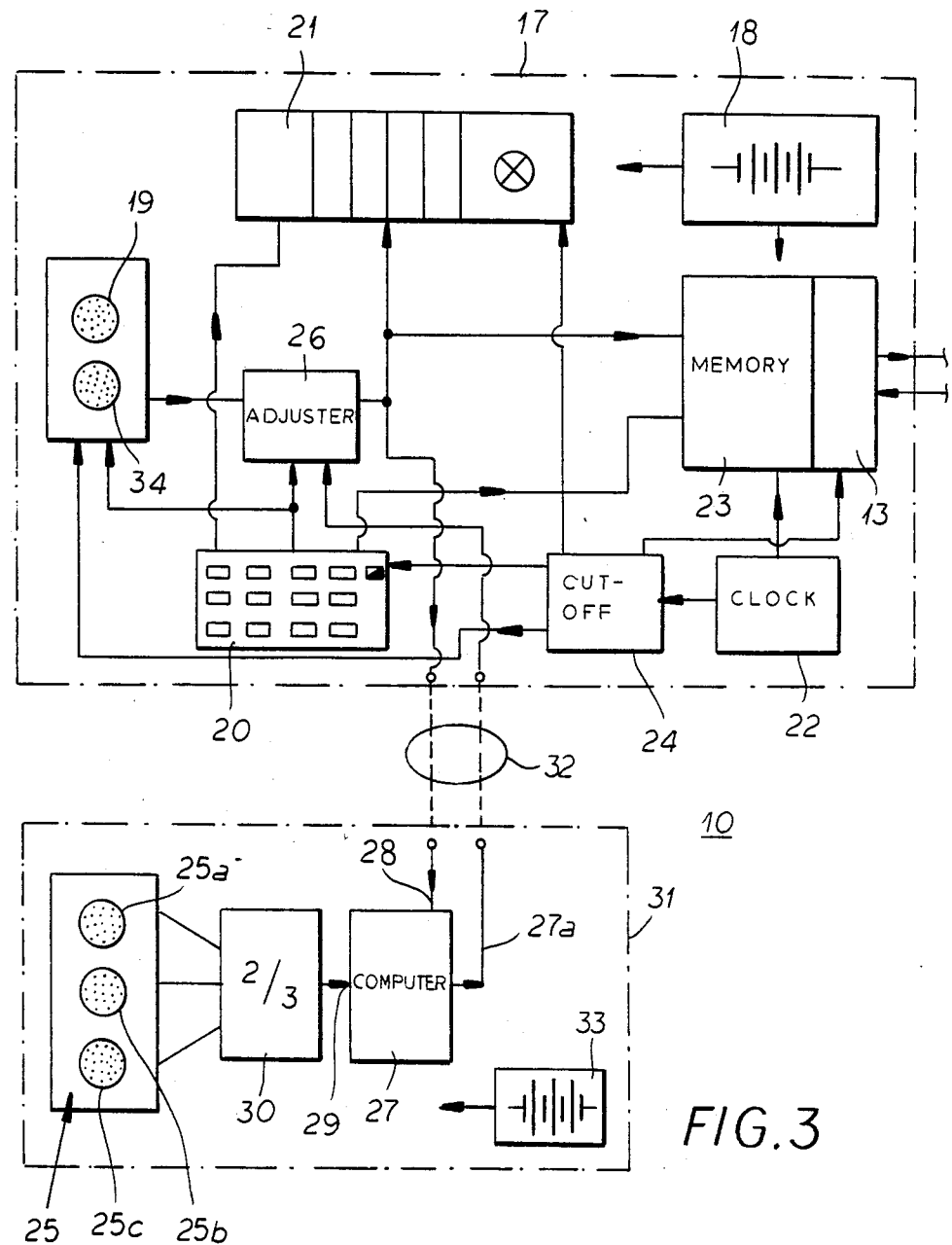
FIG. 3 is a block diagram of an apparatus embodying the present invention and utilizable in the system of FIG. 2.

FIG. 3 shows in block diagram form a measuring device 10 which can be utilized for the purposes described. According to this invention, the measuring unit 10 comprises a first measuring device 17 for the continuous measurement of at least one of the aforementioned parameters, especially the methane concentration. The measuring device 17 comprises a diagrammatically illustrated power source, e.g. a battery, a measuring system 19 which is responsive continuously to the methane concentration, an actuating unit 20 and a display or signal output unit 21. The measuring system 19 can comprise a measuring chamber, a pump for drawing gas samples through this chamber, additional chambers if desired and the appropriate detector means within this chamber.

The measuring device 17 also generally comprises a time base element 22, referred to as a clock, a data storage unit or memory 23, a cut-off switch 24 and a data preparation and transfer element 13 which can all be under the control of a microprocessor and central processing unit which has not been shown and which is built into the unit.

The unit 17 is associated with a second measuring device 31 which includes a second measuring system 25 which can be switched on at predetermined time intervals, preferably periodically.

The first measuring system 19 is also provided with an adjusting unit 26 for the setting of a function parameter of the measuring system 19, i.e. the zero point and the sensitivity or slope of the characteristic curve. The second measuring system 25 is associated with a comparator 27 whose output 27a is applied to the adjuster 26 for shifting the function parameter in a sense tending to reduce the difference or error appearing at the output of this comparator.

One input 28 to this comparator is derived from the first measuring system and represents its set point input. A second input 29 is derived from the second measuring system 25 and represents the set point input. The comparator, of course, compares these two inputs and delivers the difference signal to the line 27a to serve as the adjustment signal for the first measuring system.

FIG. 3 also shows that the second measuring system 25 include three separate detectors 25a, 25b and 25c or measuring systems, connected in parallel to a ⅔ selector circuit 30 which averages the two closest of the value 3c and supplies the result as the set point signal to the comparator. The result is a ⅔ multichannel measuring system which ignores the third or most divergent value. This represents a redundant measuring system with high measurement precision.

As is also apparent from FIG. 3, the second measuring system 25 is arranged in a separate second measuring unit 31 which can be connected to the first unit 17 by a cable connector represented diagrammatically at 32 for data transfer between the units. The second unit has its own electric current source 33. A separate actuating element for the second unit is not required since the clock 22 and the setting device or keyboard 20 of the first unit can select the time intervals at which the second unit periodically compares its output with the first. Alternatively, by simply connecting the second unit with the first, a comparison sampling can be effected upon disconnection of the two units and the movement of the second unit to another first unit along the gallery, recalibration and resetting of the first systems and a succession of units can be carried out periodically, e.g. with a period of about a week between such recalibrations. A further measuring system 34 can also be provided in the first unit for emergency use and can have less accuracy and sensitivity than the second measuring system. The cutoff device 24, upon the development of a dangerous condition and/or a defect in the measuring system 19 can automatically turn on the replacement sensor 34 and cut off the sensor 19 and, conversely can restore the sensor 19 to operation and cut off the sensor 34.

In principle, therefore, at periodic time intervals the second unit 31 is connected to the first unit 17 of the measuring device 10. The second measuring unit supplies a highly accurate set point value, which may also involve catalytic combustion detection of methane concentration, made even more precise because of the ⅔ multichannel selection. The high precision set point is compared with the actual value and the zero point and sensitivity of the first unit are adjusted accordingly. Once the correction is complete, the second unit 31 can be disconnected and moved to another location for repetition of the process.

By providing a permanent connection in place of the connector 32, the two units can be integrated with one another, advantageously, the connector 32 can be so provided that when the connection is made, the unit 31 is automatically turned on and when the two units are disconnected, the unit 31 is automatically turned off. In the event of an unsatisfactory operation of the first measuring system and/or the attainment of correction limits of this first measuring system, the measuring system 25 can be cut in for continuous outputting of the methane concentration.

I claim:

1. A method of measuring and evaluating a parameter of an atmosphere which comprises the steps of:
   continuously determining the magnitude of said parameter with a first measuring system sensitive to said parameter;
   at time-spaced intervals measuring said parameter and determining the magnitude thereof with a second measuring system sensitive to said parameter and producing an output signal; and
   adjusting at least one functional state of said first measuring system in response to said signal.

2. The method defined in claim 1 wherein at least one of the zero point and the sensitivity of said first measuring system are corrected in response to said signal over said inverval.

3. The method defined in claim 2 wherein said functional state is corrected in response to said signal automatically.

4. The method defined in claim 1 wherein said first and second measuring systems detect said parameter utilizing the same measuring principle.

5. The method defined in claim 1 wherein said first measuring system produces an output, further comprising the step of substituting the second measuring system for said first measuring system to produce said output upon the development of an undesirable operating condition of said first measuring system.

6. The method defined in claim 1 wherein said second measuring system operates under a more expensive and precise detection principle than said first measuring system.

7. The method defined in claim 1 wherein at least one of said measuring system includes a ⅔ multichannel measuring system.

8. A device for measuring and evaluating a parameter of a mine atmosphere which comprises:
- a first measuring system exposed to said atmosphere and responsive to said parameter for continuously measuring the magnitude thereof and reporting said magnitude;
- a second measuring system connectable to detect said parameter at time-spaced intervals for producing an output representing the magnitude of said parameter; and
- a means responsive to said output of said second measuring system for controlling a functional state of said first measuring system.

9. The device defined in claim 8 wherein said first measuring system is provided with a unit for controlling a functional state selected from the group which consists of zero point, sensitivity and slope of measurement curve, said means responsive to said output being connected to said unit.

10. The device defined in claim 9 wherein said means responsive to said unit includes said point/actual value comparator receiving a set point signal from said output of said second measuring system and an actual value signal from said first measuring system.

11. The device defined in claim 10 wherein at least one of said measuring systems includes a ⅔ multichannel measuring system.

12. The device defined in claim 8 wherein said second measuring system is integrated with said first measuring system and is only periodically turned on.

13. The device defined in claim 8 wherein said second measuring system is included in a unit separate from a unit provided with said first measuring system and, means being provided for connecting said units together and disconnecting said units from one another.

14. The device defined in claim 13 wherein the last mentioned means includes means for signal tranfer between said units.

15. The device defined in claim 13 wherein each of said units has a respective electric current source.

16. The device defined in claim 13 wherein said unit of said second measuring system is automatically turned on upon connection of said unit of said first measuring system and is automatically turned off upon disconnection therefrom.

* * * * *